(12) United States Patent
Dally

(10) Patent No.: US 12,137,826 B1
(45) Date of Patent: Nov. 12, 2024

(54) GLOVE CARTRIDGE ASSEMBLIES FOR TOUCHLESS GLOVE APPLICATION SYSTEMS

(71) Applicant: James Edwin Dally, Kalamazoo, MI (US)

(72) Inventor: James Edwin Dally, Kalamazoo, MI (US)

( * ) Notice: Subject to any disclaimer, the term of this patent is extended or adjusted under 35 U.S.C. 154(b) by 0 days.

(21) Appl. No.: 18/196,215

(22) Filed: May 11, 2023

(51) Int. Cl.
| | |
|---|---|
| *A47G 25/90* | (2006.01) |
| *A41D 19/00* | (2006.01) |
| *A61B 42/40* | (2016.01) |
| *A61B 42/50* | (2016.01) |

(52) U.S. Cl.
CPC ....... *A47G 25/904* (2013.01); *A41D 19/0055* (2013.01); *A61B 42/40* (2016.02); *A61B 42/50* (2016.02)

(58) Field of Classification Search
CPC ........ A47G 25/904; A61B 42/40; A61B 42/50
See application file for complete search history.

(56) References Cited

U.S. PATENT DOCUMENTS

| 4,002,276 A * | 1/1977 | Poncy | A61B 42/50 |
| | | | 223/111 |
| 4,275,812 A * | 6/1981 | Poncy | A47G 25/904 |
| | | | 223/111 |
| 4,889,266 A * | 12/1989 | Wight | A61B 42/40 |
| | | | 223/111 |
| 4,909,413 A * | 3/1990 | McCutcheon | A47G 25/904 |
| | | | 221/25 |
| 6,375,034 B1 * | 4/2002 | Corbett | A61B 42/50 |
| | | | 221/45 |
| 8,678,252 B2 * | 3/2014 | Kelly | A61B 42/40 |
| | | | 223/111 |
| 10,098,699 B1 * | 10/2018 | Buck | A61B 42/40 |
| 11,617,629 B2 * | 4/2023 | Shalom Avshalom | |
| | | | A61B 42/50 |
| | | | 223/111 |
| 2022/0202221 A1 * | 6/2022 | Shafran | A61B 42/40 |
| 2022/0233008 A1 * | 7/2022 | Waineo | A47G 25/904 |
| 2023/0032175 A1 * | 2/2023 | Brett | A47G 25/904 |

FOREIGN PATENT DOCUMENTS

DE          4125037 A1 *  2/1993 ............. A61B 42/40

* cited by examiner

*Primary Examiner* — F Griffin Hall
(74) *Attorney, Agent, or Firm* — Vorys, Sater, Seymour and Pease LLP

(57) ABSTRACT

A glove application system includes a glove application module providing a housing that defines an install cavity and an access aperture providing access into the install cavity, a pressure system operable to generate negative pressure in the install cavity, and a glove cartridge assembly mounted to the housing and including a cartridge belt having a plurality of glove cartridges spaced along the cartridge belt, each glove cartridge having a glove releasably secured to the cartridge belt with a fastening system that includes a raised section protruding from the cartridge belt and defining an internal aperture, and a lip laterally protruding from the raised section and sized to receive a wrist bead of the glove, wherein negative pressure generated by the pressure system causes the glove of an aligned glove cartridge to inflate into the install cavity.

17 Claims, 8 Drawing Sheets

GLOVE CARTRIDGE ASSEMBLIES FOR TOUCHLESS GLOVE APPLICATION SYSTEMS

BACKGROUND

The use of disposable gloves (e.g., latex gloves, nitrile gloves, etc.) is commonplace in many industries, and is generally recognized as one of the primary safeguards against inadvertent or accidental cross-contamination between a user (wearer) and the surrounding environment. When used properly, gloves improve hygiene and can minimize exposure for both the user and others, especially those serviced by the person wearing the gloves.

However, common errors that occur during glove application (placement or "donning") can compromise the overall effectiveness of glove use, such as allowing the exterior of the gloves to undergo significant physical contact prior to and during application. For example, gloves are commonly packaged in a manner that increases the probability that a user will physically contact multiple gloves with bare hands upon extracting a single glove. Moreover, the first glove is typically applied with a non-gloved hand, thereby possibly contaminating the exterior of the first glove. In effect, simply putting disposable gloves on manually can inadvertently contaminate multiple gloves intended for sterile or sanitary applications. Moreover, gloves can be contaminated through inadvertent or intentional contact with non-sanitary surfaces prior to the intended use.

Furthermore, in view of the COVID-19 pandemic that currently plagues our world, the use of disposable gloves has exponentially increased. Systems and methods of applying disposable gloves without increasing or propagating contamination is, therefore, greatly desired.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to glove application systems for applying disposable gloves and, more particularly, to spooling glove cartridges for automated glove application systems.

The automated glove application systems described herein enable "touchless" self-donning (installation) of disposable gloves and thereby minimize or eliminate user contact with the external surfaces of the glove during the application process. The systems and methods discussed herein can enhance aseptic technique and increase the speed of glove application, while simultaneously preventing contamination associated with user error and inadvertent contaminating contact with the gloves. The glove application systems incorporate individually packaged and sterilized gloves that can be accessed by the user via an automated system. Individually packaged gloves may be provided in a pre-packaged, sterilized cartridge assembly that can easily be installed into the dispenser systems described herein. The cartridge assembly may include a raised lip with a plurality of indentations, cuts, or other depressions for flexibility and ease of application. Further, one or more retaining members may be included on the cartridge assembly that can maintain the gloves in a packaged state prior to application.

The presently-disclosed embodiments are advantageous in view of the current, but waning, COVID-19 pandemic. In particular, personal protective equipment (PPE), such as disposable gloves, is prone to rapid contamination and is typically discarded once contaminated, either on purpose or inadvertently. The automated glove application systems described herein can help reduce the amount of wasted disposable gloves that may be accidentally compromised, which would otherwise require the user to discard the contaminated glove and don or apply a new glove. The automated glove application systems may be particularly advantageous in settings where a high degree of sanitation or sterilization is required or desired such as, but not limited to, hospitals, nursing homes, restaurants, bathrooms, public transportation, fueling stations, etc. The embodiments disclosed herein may facilitate function of one or more automated glove application systems which utilize a spooled glove cartridge assembly. As used herein, the terms "don" and "donning" refer to the act of applying or installing a glove on a hand. The terms "don" and "donning" may be interchangeably used with terms such as "apply" or "install".

Figure 1:
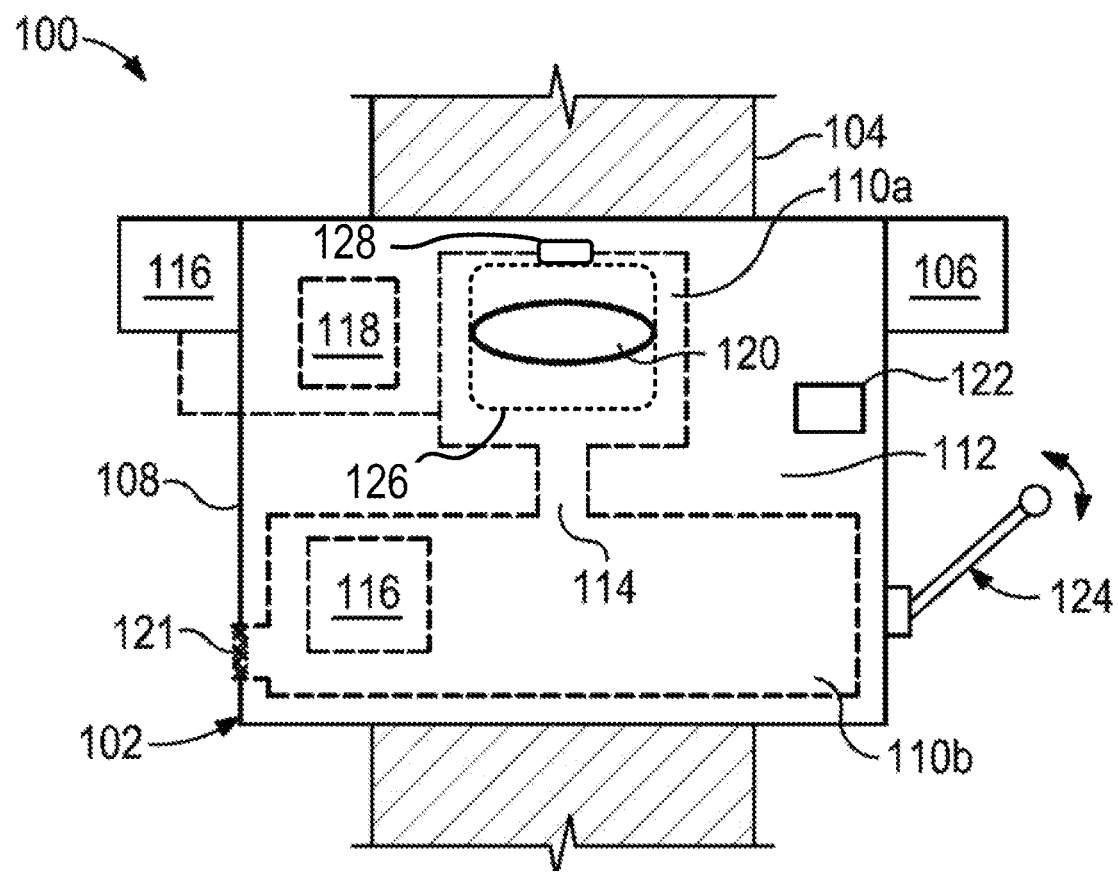
FIG. 1 is a schematic front view an example glove application system, according to one or more embodiments.

FIG. 1 is a schematic front view of an example glove application system 100, according to one or more embodiments. As illustrated, the glove application system 100 (hereafter "the system 100") may include a glove application module 102. In some embodiments, the glove application module 102 may comprise a standalone system that may be portable to any desired location. In other embodiments, however, the glove application module 102 may be mounted to a rigid structure 104 for use. The rigid structure 104 may comprise a variety of stationary structures such as, but not limited to, a wall, a countertop, a stand, a public access point (e.g., a gas pump, a subway entrance, an elevator wall, etc.), or any combination thereof. Alternatively, the rigid structure 104 may comprise a movable (transportable) structure, such as a wheeled cart, an emergency vehicle, or any combination thereof.

In some embodiments, a source of power may be included with the rigid structure 104 to operate the glove application module 102, such as electrical grid power available through a wall power outlet (e.g., 110V), or electrical power derived from a vehicle power port, etc. In embodiments where the glove application module 102 is affixed to a piece of equipment, such as a gas pump, an elevator, etc., the electrical power may be derived from such equipment. Alternatively, or in addition thereto, the glove application module 102 may include a localized power source 106, such as one or more batteries (e.g., 12V, 24V, etc.), fuel cells, a solar panel power system, or any combination thereof.

The glove application module 102 includes a housing 108 that contains or supports various devices or mechanisms used to operate the glove application module 102. In some embodiments, the housing 108 provides or otherwise defines a first or "install" cavity 110a and a second or "pressure" cavity 110b separated from the install cavity 110a by a partition 112. The cavities 110a,b may alternately be referred to as "zones". The partition 112 separates the first and second cavities 110a,b but also defines a pressure vent 114 that provides fluid (air) communication between the first and second cavities 110a,b.

The glove application module 102 may also include a pressure system 116 (shown in dashed lines) operable to generate cyclical negative and positive pressure conditions in the install cavity 110a. The negative and positive pressures are measured with respect to ambient or atmospheric pressure. Accordingly, negative pressure generation provided by the pressure system 116 may comprise any pressure condition within the install cavity 110a that is lower than atmospheric pressure, and positive pressure generation may comprise any pressure condition within the install cavity 110a that is higher than atmospheric pressure.

In some embodiments, the pressure system 116 may be arranged within the pressure cavity 110b and may be operable to generate negative and positive pressure conditions in the install cavity 110a via the pressure vent 114. In such embodiments, the pressure system 116 may generate cyclical negative and positive pressure within the pressure cavity 110b, and such pressure changes will be communicated to the install cavity 110a via the pressure vent 114. More specifically, the pressure system 116 may be configured to generate a low pressure condition within the pressure cavity 110b that draws air from the install cavity 110a and into the pressure cavity 110b via the pressure vent 114. The pressure system 116 may then be configured to generate a high pressure condition within the pressure cavity 110b that forces air into the install cavity 110a via the pressure vent 114. In at least one embodiment, the install cavity 110a may be substantially sealed to enhance the effects of the cyclical negative and positive pressure conditions.

Alternatively, the pressure system 116 may communicate directly with the pressure vent 114 via a hose or the like, thus not affecting pressure conditions in the pressure cavity 110b, but only within the install cavity 110a. In other embodiments, however, the pressure system 116 may be arranged outside of the pressure cavity 110b, such as being attached to the exterior of the housing 108. In such embodiments, the pressure cavity 110b may be omitted as unnecessary, and the pressure system 116 may fluidly communicate directly with the install cavity 110a through a sidewall of the housing 108, for example, to generate the negative and positive pressure conditions in the install cavity 110a.

The pressure system 116 can include any suitable compressor, pump, or device capable of increasing and decreasing the pressure within the install cavity 110a. Suitable examples for the pressure system 116 include, but are not limited to, a pressure piston, an air piston, a plunger, a wiper, a collapsible/deformable mechanism (e.g., a bellows, an accordion-type bellows, an expandable bladder, etc.), a reversing compressor or pump, or any combination thereof. In at least one embodiment, the pressure system 116 may comprise a spring-loaded bellows that may be actuated in one direction to create a positive pressure condition, and allowed to revert back to its natural state while creating a negative pressure condition. In some embodiments, air may be drawn in by the pressure system 116 from the exterior of the housing 108 to increase the pressure within the install cavity 110a. In such embodiments, a vent 121 may be defined in a sidewall of the housing 108 and an inlet filter may be arranged within the vent 121 to filter the incoming air. The inlet filter may be a high efficiency particulate air (HEPA) filter configured to trap a variety of contaminants prior to entering the glove application module 102 and, more particularly, the install cavity 110a.

The glove application module 102 may further include a glove cartridge assembly 118 (shown generally in dashed lines) mounted to the housing 108 and including a plurality of individually packaged and releasably secured gloves. The gloves may comprise disposable gloves such as, but not limited to, latex gloves, nitrile gloves, butyl gloves, vinyl gloves, neoprene gloves, or any combination thereof. The gloves may be sterile or non-sterile. As discussed in more detail below, the gloves in the glove cartridge assembly 118 may be individually packaged and/or spaced along a cartridge belt configured to be driven (transferred) between opposing supply and recovery spools. The glove application module 102 may include means for selectively advancing individual gloves in the glove cartridge assembly 118 to align with an access aperture 120 defined in the housing 108. The access aperture 120 provides a location where a user may be able to insert a hand into the install cavity 110a via the access aperture 120 and simultaneously insert the hand into a glove aligned with the access aperture 120.

In some embodiments, as illustrated, the glove cartridge assembly 118 may be arranged within the install cavity 110a. In other embodiments, however, the glove cartridge assembly 118 may be attached to the exterior of the housing 108 and the cartridge belt may be fed into the housing 108 on one side from an externally-mounted supply spool, and received by an externally-mounted recovery spool on an opposing side of the housing 108.

In some embodiments, the glove application module 102 may further include a user interface 122 designed to allow a user to operate the glove application module 102. In some embodiments, the user interface 122 may comprise a touch interface, such as a self-sanitizing switch or button mounted to the housing 108. In such embodiments, a user may manually flip the switch or press the button to activate operation of the glove application module 102, which may cause the glove cartridge assembly 118 to advance the cartridge belt and align a glove with the access aperture 120. In other embodiments, the user interface 122 may comprise a graphical user interface (GUI), such as a self-sanitizing touch-screen display that allows a user to operate the glove application module 102. In such embodiments, the user interface 122 may be programmed to accept user input for various glove selection criteria such as, but not limited to, glove size, glove color, glove material, glove style, right hand, left hand, or any combination thereof.

In yet other embodiments, the user interface 122 may comprise a touchless interface. In such embodiments, for example, the touchless user interface 122 may comprise one or more sensors that facilitate touchless operation of the glove application module 102. More particularly, various sensors incorporated into the glove application module 102 may sense movement or motion in proximity of the user interface 122 (e.g., waving a hand in front of the user interface 122, approaching the glove application module 102, etc.). Such movement or motion in proximity of the user interface 122 may cause the glove cartridge assembly 118 to advance and align a glove with the access aperture 120. Suitable sensors for the user interface 122 include, but are not limited to, motion sensors (e.g., infrared (IR) sensors), photoelectric sensors (e.g., photo eyes), light curtains, light sensors, proximity sensors (e.g., radio-frequency identification (RFID) readers), or any combination thereof. In at least one embodiment, the touchless user interface 122 may comprise a proximity sensor employing RFID technology, for example, which may detect a user's identification (e.g., a company badge or the like) once in proximity of the glove application module 102. In other embodiments, the touchless user interface 122 may comprise a voice-activated computer system with a microphone and speaker(s). In such embodiments, the user may speak voice commands to the user interface 122 to cause the glove cartridge assembly 118 to advance and align a glove with the access aperture 120.

In some embodiments, one or both of the pressure system 116 and the glove cartridge assembly 118 may be powered by the localized power source 106. In other embodiments, one or both of the pressure system 116 and the glove cartridge assembly 118 may be powered with electrical grid power available through a wall power outlet (e.g., 110V), or electrical power derived from a vehicle power port. In yet other embodiments, however, a mechanical actuator 124 may form part of the user interface 122 and may be manually actuated by the user to operate the glove application module 102. Such embodiments may prove advantageous in the event grid power or the localized power source 106 is unavailable, such as in remote or portable applications where ready access to electrical power may be limited.

The mechanical actuator 124 may comprise, for example, one or more levers or pedals that a user must manually actuate (e.g., reciprocate) to operate the glove cartridge assembly 118 and/or the pressure system 116. In the illustrated embodiment, the mechanical actuator 124 comprises a lever that can be pivoted up or down by a user to operate the glove application module 102. In at least one embodiment, the lever may comprise a "wrist blade" or the like, which comprises a generally flat surface that a user may actively engage with an arm, a wrist, etc. to manually actuate the glove cartridge assembly 118 and/or the pressure system 116 without having to use their hands. In other embodiments, the mechanical actuator 124 may comprise a treadle having a geared and/or pulley interconnection with one or both of the glove cartridge assembly 118 and the pressure system 116, and user actuation (operation) of the treadle may cause the glove cartridge assembly 118 and/or the pressure system 116 to operate.

Example operation of the glove application module 102 is now provided. In some embodiments, a user may activate operation of the glove application module 102 through interaction with the user interface 122 and/or the mechanical actuator 124, as generally discussed above. In such embodiments, operating the user interface 122 (e.g., touch or touchless) and/or the mechanical actuator 124 may cause the glove cartridge assembly 118 to advance a cartridge belt and align a glove with the access aperture 120. Once the glove is aligned with the access aperture 120 (or as the glove is being moved and aligned), the pressure system 116 may be activated to generate negative pressure (e.g., a vacuum) within the install cavity 110a. The generated negative pressure may be sufficient to inflate the aligned glove into the interior of the install cavity 110a, but each glove may be operatively coupled to the cartridge belt such that inflating the glove into the install cavity 110a does not release the glove from the cartridge belt. In other embodiments, however, the user must first penetrate a seal that covers the glove before the glove can be inflated into the install cavity 110a, without departing from the scope of the disclosure.

Once the glove is inflated and extended into the install cavity 110a, the user may extend a hand into the inflated glove via the access aperture 120, at which point the pressure system 116 may cycle (switch-return cycle) from generating negative pressure to generating positive pressure within the install cavity 110a. Cycling the pressure system 116 from negative to positive pressure generation may be manually or electronically controlled. In embodiments where the pressure system includes a reciprocating device, such as a spring-loaded bellows, an air piston, or a treadle, cycling the pressure system 116 from negative to positive pressure generation may naturally occur during operation. In some embodiments, the duration of the negative/positive pressure cycle may be based on a selected timing, such as every 2 seconds, 3, seconds, 5 seconds, etc. In other embodiments, cycling the pressure system 116 from negative to positive pressure may be triggered by operation of one or more internal sensors that detect the presence of the hand. In such embodiments, a motion sensor or a light curtain may cause the pressure system 116 to switch (cycle) from negative to positive pressure within the install cavity 110a once the presence of a hand within the inflated glove is detected. In some embodiments, the pressure system 116 may continuously operate, either cycling between negative and positive pressure conditions, or maintaining a negative pressure within the install cavity 110a. In other embodiments, however, the pressure system 116 may only be operated as needed to install a glove, following which operation of the pressure system 116 may cease.

The positive pressure generated by the pressure system 116 may help seat the glove onto the user's hand and thereby provide tactile feedback to the user that the glove is properly donned (installed). Without the positive pressure forces that help seat the glove on the user's hand, a user may be able to withdraw the hand without removing the glove, thus defeating the purpose of the glove application module 102. Accordingly, once the user feels that the glove is properly applied (seated) on the hand from the positive pressure condition, the now-gloved hand may be withdrawn from the access aperture 120. In some embodiments, withdrawing the gloved hand from the access aperture 120 may release the glove from the cartridge belt. In other embodiments, or in addition thereto, the positive pressure condition may create sufficient detachment forces to release the glove from the cartridge belt.

In some embodiments, withdrawing the gloved hand from the install cavity 110a may trigger operation of the glove cartridge assembly 118 to advance and align another glove with the access aperture 120. In such embodiments, the default position for the glove application module 102 may be to have a glove already advanced and aligned with the access aperture 120 before a user approaches the system 100. Accordingly, once a glove is dispensed from the glove application module 102 and the user withdraws the hand, the glove cartridge assembly 118 may automatically advance and align another glove with the access aperture 120, thus readying the glove application module 102 for subsequent and continued use.

In some embodiments, the system 100 may include a door 126 which may close over the access aperture 120 following removal of a gloved hand from the system 100. One or more signals from the sensors of the user interface 122, or actuation of the mechanical actuator 124, may signal a motor 128 that a gloved hand has been removed and that a new glove cartridge is required. As such, the motor 128 may slide the door 126 over the access aperture 120 and otherwise occlude the access aperture 120 to seal off the install cavity 110a. Following closure of the access aperture 120, a new glove cartridge may be advanced into the install cavity 110a. Once a signal indicates a received glove cartridge, the motor 128 may slide the door 126 out of the access aperture 120, and the system 100 may be ready to seat a new glove onto an operator. This sealing of the system 100 during advancement of a new glove cartridge may further protect the gloves from foreign contaminants.

Figure 2:
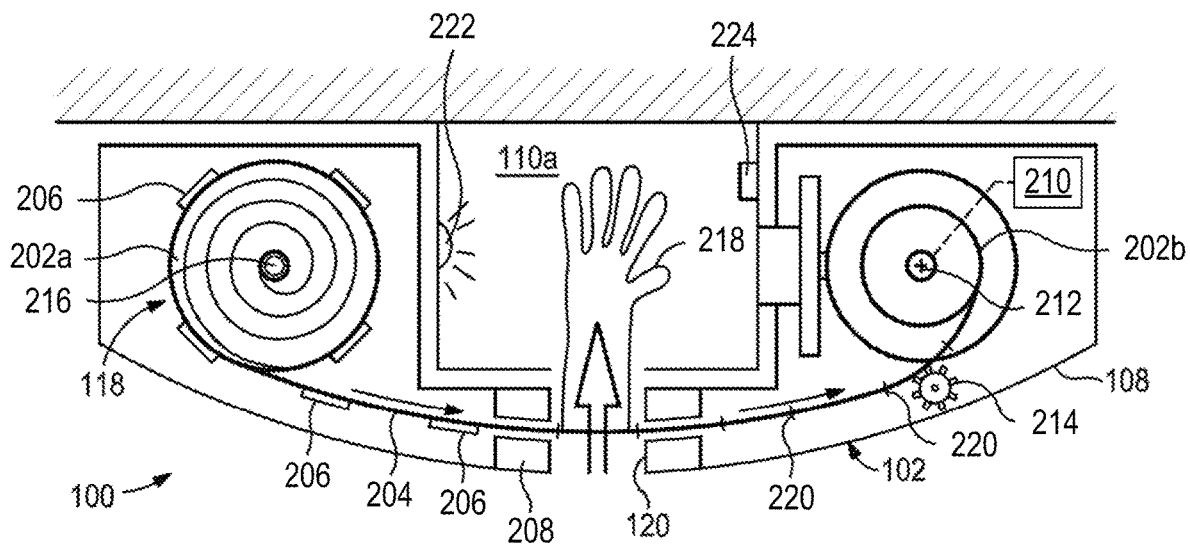
FIG. 2 is an exposed top view of the glove application system of FIG. 1, according to one or more embodiments of the disclosure.

FIG. 2 is an exposed top view of the system 100 of FIG. 1, according to one or more embodiments of the disclosure. As illustrated, the glove cartridge assembly 118 may include a supply spool 202a, a recovery spool 202b, and a radial cartridge belt 204 extendable between the supply and recovery spools 202a,b. The cartridge belt 204 may be preloaded with a plurality of individually spaced and separated glove cartridges 206 attached to the cartridge belt 204 at predetermined locations and spacing. Each glove cartridge 206 includes a single glove and a means of attaching the glove to the cartridge belt 204. In some embodiments, the glove may be vacuum-packed and sealed within sterilized packaging, but could alternatively not include any packaging and instead merely be attached to the cartridge belt 204. The cartridge belt 204 can have a stipulated number of glove cartridges 206 affixed thereto such as, but not limited to, 25, 50, 100, 200, any number between 25 and 200, less than 25, or more than 200.

Before the glove cartridge assembly 118 is installed in or on the glove application module 102, the cartridge belt 204 may be sterilized and pre-packaged for delivery. In some embodiments, the pre-packaged and sterilized cartridge belt 204 may be entirely (or mostly) pre-wound onto the supply spool 202a, but could alternatively be installed on an existing supply spool 202a forming part of the system 100.

In some embodiments, installing the glove cartridge assembly 118 may entail merely attaching the glove cartridge assembly 118 to the glove application module 102 such that the cartridge belt 204 extends across the access aperture 120. In such embodiments, the glove cartridge assembly 118 may be provided to the user with the cartridge belt 204 already extending between the supply and recovery spools 202a,b. In other embodiments, however, it is contemplated herein that a user will be able to install the glove cartridge assembly 118. In such embodiments, one end of the cartridge belt 204 is pulled radially from the supply spool 202a, extended (threaded) through an alignment guide 208 provided within the housing 108, and operatively coupled to the recovery spool 202b such that driving rotation of the recovery spool 202b will correspondingly pull additional length of the cartridge belt 204 from the supply spool 202a and through the alignment guide 208. As illustrated, the alignment guide 208 is aligned with the access aperture 120, and advancing (pulling) the cartridge belt 204 through the alignment guide 208 will allow individual glove cartridges 206 to be sequentially aligned with the access aperture 120 for operation.

In some embodiments, the recovery spool 202b may be driven in rotation by a motor 210 configured to rotate the recovery spool 202b about a rotational axis 212. In such embodiments, the motor 210 may be operated to advance the cartridge belt 204 through the alignment guide 208 at predetermined increments that accurately and precisely align individual glove cartridges 206 with the access aperture 120. In other embodiments, however, or in addition thereto, the glove application module 102 may further include one or more pinion gears 214 engageable with the cartridge belt 204 and rotatable to advance the cartridge belt 204 through the alignment guide 208 at predetermined increments to align individual glove cartridges 206 with the access aperture 120. In such embodiments, gear teeth of the pinion gear 214 may mate with corresponding holes defined in the cartridge belt 204 such that rotation of the pinion gear 214 drives the gear teeth against the corresponding holes and advances the cartridge belt 204. Moreover, in such embodiments, the recovery spool 202b may not be required, but instead the used portion of the cartridge belt 204 may self-coil on the opposite side of the housing 108 past the pinion gear(s) 214.

Those skilled in the art, however, will readily appreciate that various other ways may be employed to advance the cartridge belt 204, without departing from the scope of the disclosure. For example, as indicated above, in at least one embodiment, a mechanical actuator 124 (FIG. 1) may be included and manually actuated by the user to operate the glove application module 102; e.g., the glove cartridge assembly 118.

In example operation, the cartridge belt 204 is advanced from the supply spool 202a until an individual glove cartridge 206 aligns with the access aperture 120. In some embodiments, the supply spool 202a may be spring loaded and thereby generate constant tension in the cartridge belt 204. In at least one embodiment, for example, the supply spool 202a may include a torsion spring 216 that maintains a tensile load (pull) on the cartridge belt 204 and thereby keeps the cartridge belt 204 taut at all times.

Once a glove cartridge 206 is properly aligned with the access aperture 120, or as the glove cartridge 206 is moving to the access aperture 120, the pressure system 116 (FIG. 1) may be operated (activated) to generate negative pressure within the install cavity 110a. The negative pressure may be sufficient to at least partially inflate a glove 218 from the aligned glove cartridge 206 such that the glove 218 extends into the install cavity 110a. The negative pressure required to inflate the glove 218, however, may not be sufficient to release the glove 218 from the cartridge belt 204. In some embodiments, aligning the glove cartridge 206 with the access aperture 120 forms a barrier between the access aperture 120 and the install cavity 110a, and thereby forms a pressure-sensitive seal that helps inflate the glove 218. The glove 218 may be inflated from a packaged (stowed) configuration, which may include a packaged and/or compressed glove with or without an exterior seal or covering.

Once the glove 218 is inflated, the user may extend a hand into the inflated glove via the access aperture 120, and the pressure system 116 may then cycle (switch) to generating positive pressure in the install cavity 110a. As mentioned above, the positive pressure can force the glove 218 against the user's hand and thereby provide positive tactile feedback that lets the user know that the glove 218 is properly donned (applied) and ready to be withdrawn. Once the user feels that the glove 218 is properly applied, the now-gloved hand may be withdrawn from the access aperture 120, thus releasing the glove 218 from the cartridge belt 204. In some embodiments, however, and as also mentioned above, the positive pressure within the install cavity 110a may be sufficient to release of the glove 218 from the cartridge belt 204.

Upon withdrawing the now-gloved hand from the install cavity 110a, the cartridge belt 204 may be advanced until another (subsequent) glove cartridge 206 aligns with the access aperture 120. Alternatively, the cartridge belt 204 may be advanced upon re-activating the glove application module 102. In either scenario, advancing the cartridge belt 204 could be done either manually or through an automated system, as generally described herein. The recovery spool 202b may be configured to collect and/or wind the used cartridge belt 204 and corresponding empty apertures 220 where individual glove cartridges 206 were previously provided. Once the supply spool 202a is depleted of glove cartridges 206, the glove cartridge assembly 118 may be replaced with a new glove cartridge assembly. The glove application module 102 may be configured with interchangeable or refillable glove cartridge assemblies that enable quick refills that minimize potential contamination of the packaged gloves 218. The glove cartridge assembly 118 and any replacement glove cartridge assemblies may come pre-packaged, sterilized, and sealed prior to installation.

In some embodiments, the system 100 may further include a sterilizing device 222 positioned within the install cavity 110a. The sterilizing device 222 may be operable to sanitize and/or sterilize the glove 218 upon introduction (inflation) into the install cavity 110a. In some embodiments, operation of the sterilizing device 222 may be activated once the inflated glove 218 is detected within the install cavity 110a with one or more sensors 224.

Figure 3:
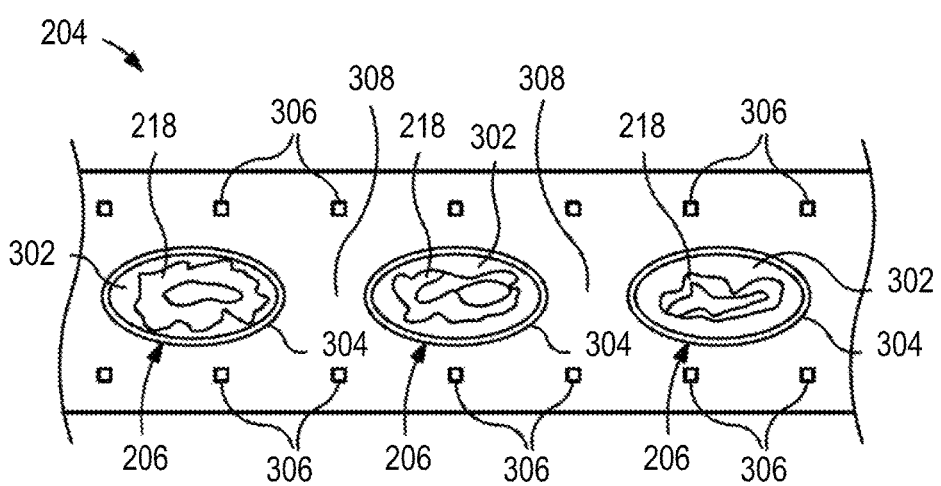
FIG. 3 is a plan view of a portion of an example embodiment of the cartridge belt of FIG. 2, according to embodiments of the present disclosure.

FIG. 3 is a plan view of a portion of an example embodiment of the cartridge belt 204. As illustrated, the cartridge belt 204 may comprise a generally planar strip of material having a plurality of glove cartridges 206 coupled thereto. The cartridge belt 204 may be made of a variety of flexible materials, such as a mechanically durable plastic (e.g., vinyl, polyethylene, etc.), but could alternatively be made of paper or a paper product. In at least one embodiment, however, the cartridge belt 204 may be made of the same material as the gloves 218.

Each glove cartridge 206 may include a glove 218 individually packaged (stowed) and releasably secured to the cartridge belt 204 in the packaged configuration. In some embodiments, each glove 218 may be vacuum packed within a sealed interface 302, such as a protective cellophane seal. In at least one embodiment, the sealed interface 302 may provide tamper proof packaging, but may be thin enough that it will easily tear upon user penetration with a hand. In other embodiments, however, the sealed interface 302 may be omitted. In either scenario, each glove 218 may be sterilized prior to installation on the cartridge belt 204, thus providing a plurality of sealed and sterilized replacement glove cartridges 206 spaced from each other along the cartridge belt 204 at known distances.

Each glove cartridge 206 may further include a fastening system 304 configured to releasably secure the glove 218 to the cartridge belt 204 in the corresponding glove cartridge 206. In some embodiments, for example, the fastening system 304 may be configured to receive and releasably secure the wrist portion of each glove 218 (e.g., the wrist bead), which helps restrain the glove 218 during inflation. In at least one embodiment, the fastening system 304 may comprise a split O-ring that releasably secures the wrist bead of the glove 218. In other embodiments, however, the fastening system 304 may comprise a releasable adhesive, a wax, a Velcro attachment, one or more mechanical staples, or any other type of releasable mechanism that can hold the glove 218 in place until the proper amount of tension is applied on the glove 218 to release it from the fastening system 304. In yet another embodiment, the fastening system 304 may comprise overlaying substrates and the wrist bead of the glove 218 may interpose the overlaying substrates in a sandwich-type arrangement that releasably secures the glove 218. The fastening system 304 may also facilitate a pressurizable seal that allows the glove 218 to be inflated into the install cavity 110a (FIGS. 1-2).

In embodiments where the glove application module 102 (FIG. 2) includes the pinion gear(s) 214 (FIG. 2), the cartridge belt 204 may define a series of equidistantly spaced holes 306 along one or both of its lateral sides. The holes 306 may be configured to mate with the gear teeth of the pinion gear 214 and, as the pinion gear 214 rotates, the gear teeth sequentially engage the holes 306 and thereby advance (drive) the cartridge belt 204 forward. Accordingly, the holes 306 may comprise equidistantly spaced notches or other indexing features configured to aid in the timing and accurate placement of the glove cartridges 206 during operation.

In some embodiments, the cartridge belt 204 may provide or otherwise define spacer sections 308 interposing longitudinally adjacent glove cartridges 206 along the length of the cartridge belt 204. During example operation in accordance with some embodiments, the cartridge belt 204 may be advanced until a spacer section 308 is aligned with the access aperture 120 (FIGS. 1-2). The aligned spacer section 308 may be configured to limit access to the install cavity 110a (FIGS. 1-2) between glove application cycles to minimize contamination. In at least one embodiment, the spacer section 308 may form a seal at the access aperture 120, which may help prevent entry of particulates and contaminants between glove application cycles.

Figure 4:
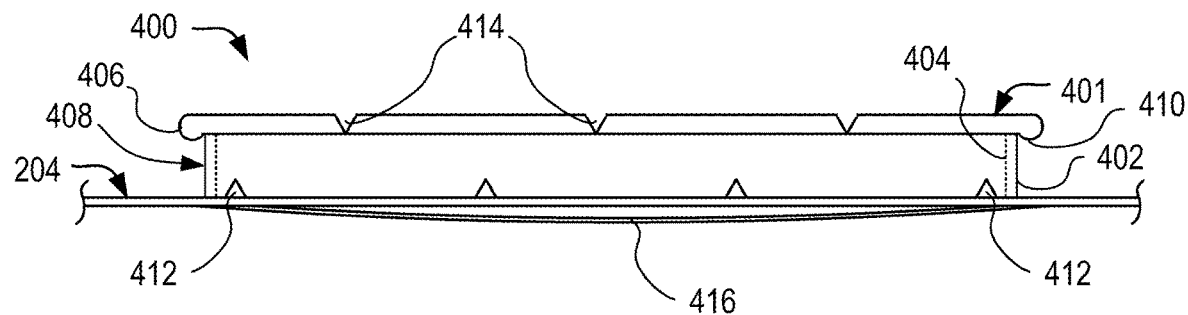
FIG. 4 is a side view of an example glove cartridge, according to one or more embodiments of the disclosure.

FIG. 4 is a side view of an example glove cartridge 400, according to one or more embodiments of the disclosure. The glove cartridge 400 may be similar in some respects to the glove cartridges 206 of FIGS. 2-3 and, therefore, may be best understood with reference thereto, where like numerals will represent like components not described again in detail. As illustrated, the glove cartridge 400 may be attached to or form a portion of the cartridge belt 204, which may comprise a generally planar strip of flexible material, such as a mechanically durable plastic (e.g., vinyl, polyethylene, etc.) or paper product. In at least one embodiment, the cartridge belt 204 is made of polypropylene or polyethylene tetrahydrate. In one or more embodiments, the glove cartridge 400 may be formed of the same material, or extruded from, the cartridge belt 204 such that the glove cartridge 400 forms an integral portion of the cartridge belt 204.

The glove cartridge 400 may define a fastening system 401 protruding from the cartridge belt 204. The fastening system 401 may include a raised section 402 which protrudes from the cartridge belt 204. The raised section 402 may define an internal aperture 404 which provides an opening for insertion of a glove (e.g., the glove 218 of FIG. 2-3) and/or hand. The raised section 402 may further define a lip 406 on an external surface 408 of the raised section. The lip 406 may protrude laterally from the external surface 408 and may present a rounded or beaded shape 410 for retention of a glove without sharp edges. The lip 406 may be sized such that the rounded or beaded shape 410 may accommodate a wrist bead of the glove and may retain the glove on the glove cartridge 400 during operation.

As the cartridge belt 204 is loaded onto one or more spools (e.g., the supply spool 202a and/or recovery spool 202b of FIG. 2), the glove cartridge 400 may need to be flexed into a convex shape to wrap around the body of the spool. Accordingly, a plurality of first relief cuts 412 may be defined at the interface between the glove cartridge 400 and the cartridge belt 204. In at least one embodiment, the plurality of first relief cuts 412 may be triangular in shape, as illustrated, such that the glove cartridge 400 may be flexed or warped (bent) during spooling. As the cartridge belt 204 and glove cartridge 400 are unspooled, the plurality of first relief cuts 412 may return to an original, unflexed shape, as shown in FIG. 4.

Conversely, as the glove cartridge 400 is received at an install cavity (e.g., the install cavity 110a of FIG. 1), the glove cartridge 400 may need to be flexed into a concave shape to prepare for donning. As such, a plurality of second relief cuts 414 may be defined at various locations along the lip 406 and/or raised section 402. As with the plurality of first relief cuts 412, the plurality of second relief cuts 414 may be triangular in shape to enable flexing or warping of the glove cartridge 400 in the desired direction. Further, the flexing or warping of the glove cartridge 400 into a concave shape may reduce the radius of the lip 406 and thus may enable easier release of an installed glove onto an operator's hand.

In at least one embodiment of the present disclosure, the glove cartridge 400 may include one or more retaining whiskers 416 at or below the cartridge belt 204. The retaining whiskers 416 may extend across the internal aperture 404 to prevent an inserted glove from protruding from the cartridge belt 204 during spooling and unspooling. However, the retaining whiskers 416 may be loosely attached, or otherwise fragile enough, to be detachable during donning or while subject to negative pressure. As such, the retaining whiskers 416 may hold a glove in place during transport without obstructing operation during donning. In some embodiments, the retaining whiskers 416 may be formed of the same material as the cartridge belt 204. In these embodiments, the retaining whiskers 416 may be punched out and defined by the cartridge belt 204 when forming the internal aperture 404, or otherwise integrally attached to the cartridge belt 204. In further embodiments, however, the retaining whiskers 416 may be formed of additional plastics or fabric strands and adhered, fastened, or otherwise attached to the cartridge belt 204 or the glove cartridge 400.

Figure 5A:
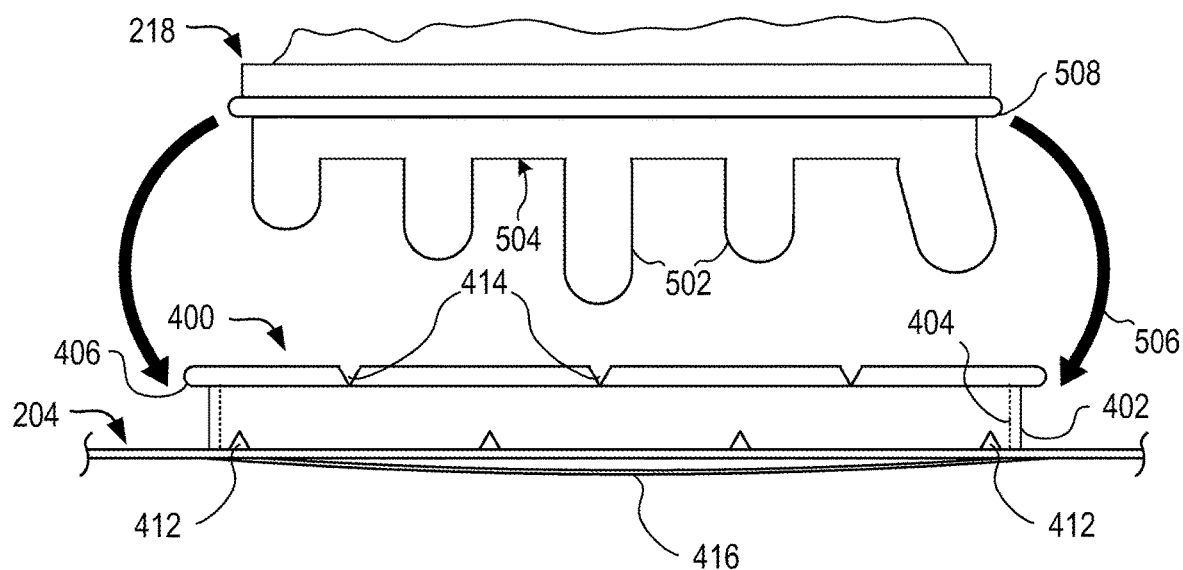
FIG. 5A is a side view of the example glove cartridge during installation of a glove, according to one or more embodiments of the disclosure.

FIG. 5A is a side view of the glove cartridge 400 during installation of a glove 218 to the glove cartridge 400, according to one or more embodiments of the disclosure. The fingers 502 of the glove 218 may be inserted through the internal aperture 404 and retained in place via the retaining whiskers 416. The outer surface 504 of the glove 218, including the wrist bead 508, may be doubled over, as shown, and stretched in direction 506 to be placed about the outer circumference of the raised section 402. The wrist bead 508 of the glove 218 may be retained in place by the lip 406, such that additional force may be required to remove the glove 218 from the fastening system 401. As the glove cartridge 400 and glove 218 are spooled for later use, the plurality of first relief cuts 412 may flex the lip 406 outward, further stretching and securing the wrist bead 508. Conversely, as the glove cartridge 400 and glove 218 are prepared for donning, the plurality of second relief cuts 414 may flex the lip 406 inward. The inward flexing of the lip 406 may reduce the force needed to release the wrist bead 508 from the lip 406, thus facilitating donning of the glove 218. Further, the retaining whiskers 416 may be severed or detached by the force of an operator's hand or any negative pressure generated against the outer surface 504 of the glove 218.

Figure 5B:
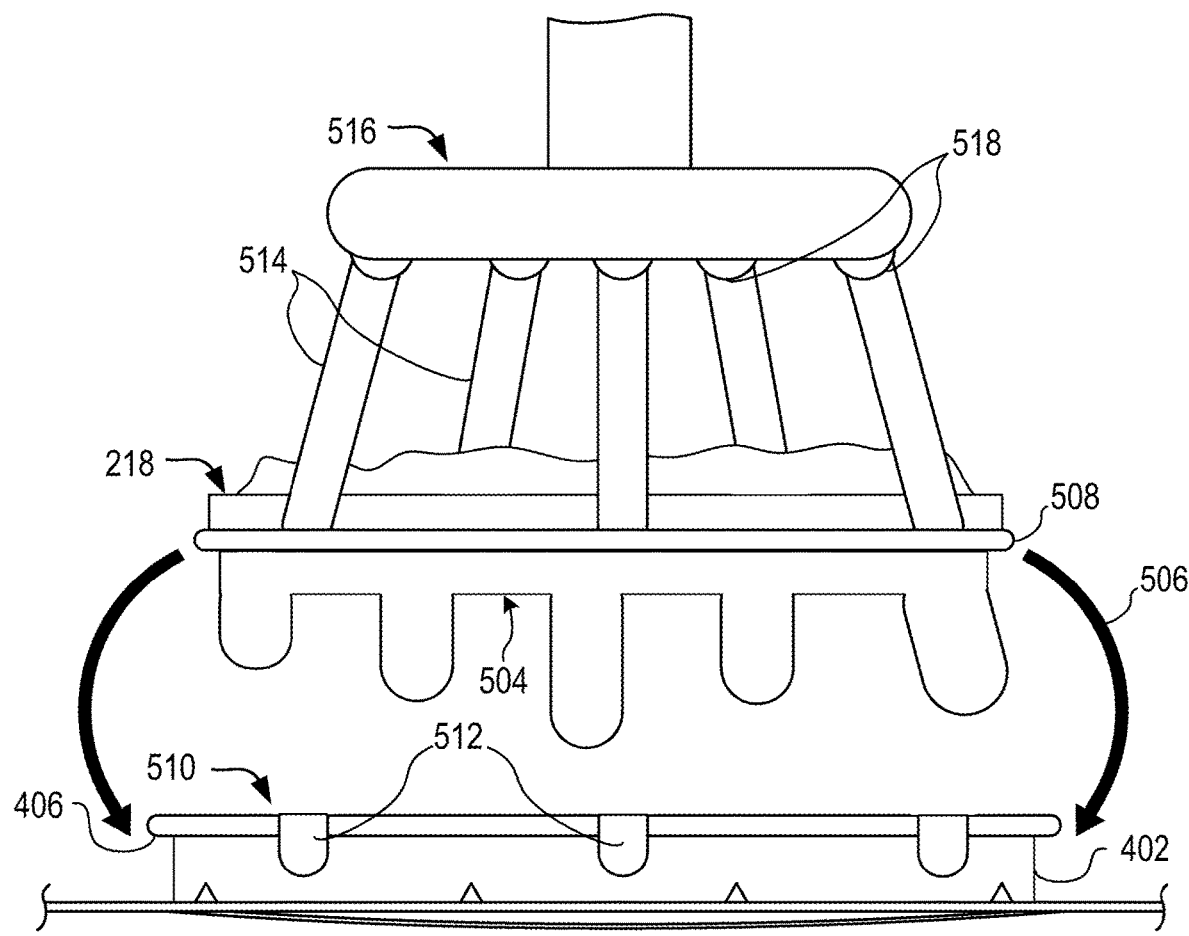
FIG. 5B is a side view of a further example glove cartridge during installation of a glove, according to one or more embodiments of the disclosure.

FIG. 5B is a side view of a further example glove cartridge 510 during installation of the glove 218 to the glove cartridge 510, according to one or more embodiments of the disclosure. The glove cartridge 510 may include similar features to the glove cartridge 400 of FIGS. 4 and 5A. However, the glove cartridge 510 may include a plurality of castellations 512 in place of, or in addition to, the plurality of second relief cuts 414 of FIGS. 4 and 5A. The plurality of castellations 512 may enable similar flexing of the glove cartridge 510, while further aiding in glove installation. The castellations 512 may be sloped or tapered towards the center of the glove cartridge 510 to define a smaller internal radius.

As shown in FIG. 5B, the castellations 512 may be sized to align with and receive a plurality of installation fingers 514 included on an assembly arm 516. The assembly arm 516 may be manually-operated or programmed for automatic robotic operation. The installation fingers 514 may be received within the wrist bead 508 of the glove 218 and then spread radially outward by one or more actuators 518 included on the assembly arm 516. As the installation fingers 514 spread radially outward, the wrist bead 508 is correspondingly forced radially outward to assume a diameter greater than that of the lip 406.

The assembly arm 516 may then lower the stretched glove 218 in the direction 506 towards the glove cartridge 510. Once the wrist bead 508 is positioned below the lip 406, the installation fingers 514 may be radially retracted by the actuators 518 to enable contact between the raised section 402 and the outer surface 504 of the glove 218 and otherwise locating the wrist bead 508 below the lip 406. The installation fingers 514 may then be operated to retract radially inwards and towards the glove cartridge 510 until being received within the castellations 512. As the installation fingers 514 enter the castellations 512, the installation fingers 514 traverse the sloped or tapered design towards a radius smaller than the lip 406 or wrist bead 508, thereby seating the wrist bead 508 against the outer circumference of the glove cartridge 510 below the lip 406. Once the installation fingers 514 are released from the glove 218, the assembly arm 516 may travel away from the glove cartridge 510.

Figure 6:
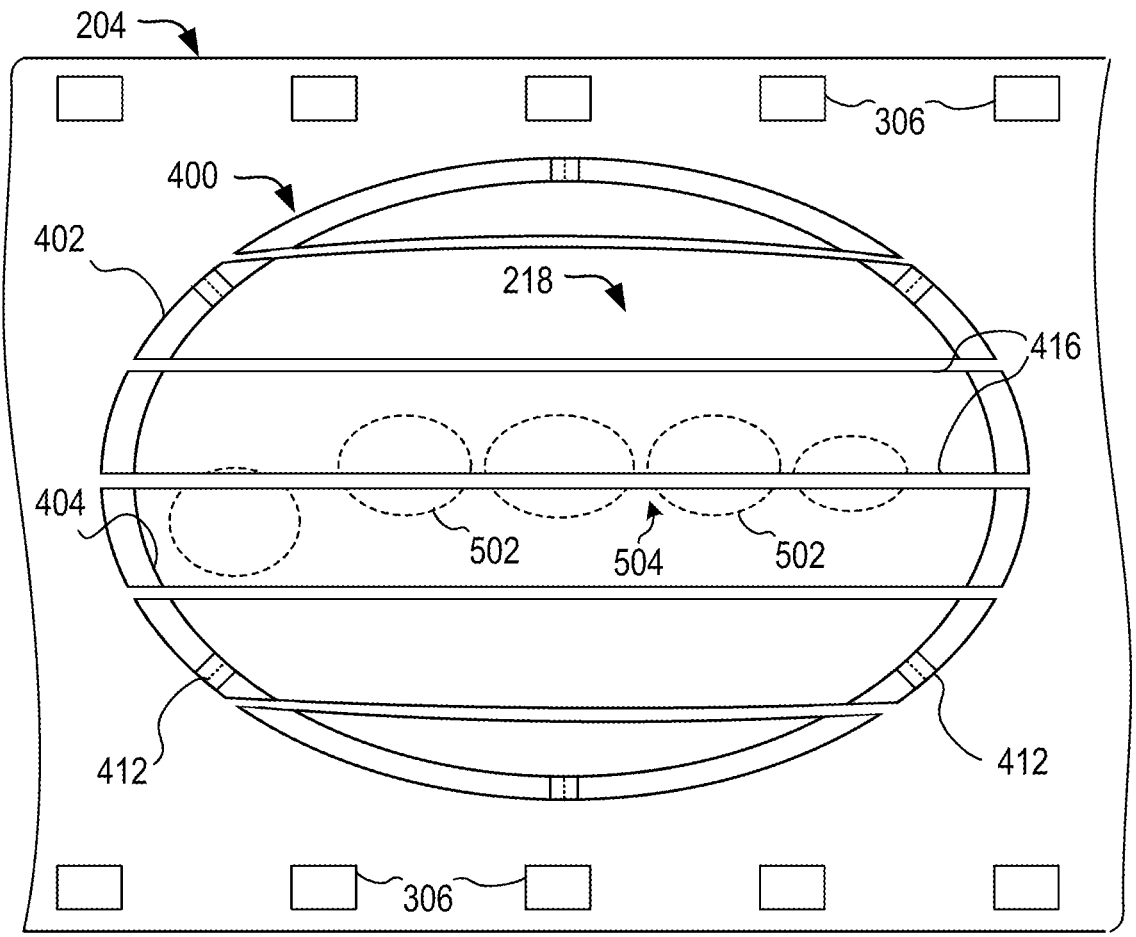
FIG. 6 is a bottom view of the example glove cartridge following installation of the glove, according to one or more embodiments of the disclosure.

FIG. 6 is a bottom view of the glove cartridge 400 following installation of the glove 218, according to one or more embodiments of the disclosure. Alternatively, the glove cartridge 400 in FIG. 6 could be replaced with the glove cartridge 510, without departing from the scope of the disclosure. The cartridge belt 204 may be seen with the plurality of holes 306 for mating with one or more gear teeth to be used during spooling and unspooling. A bottom surface of the raised section 402 may be seen with the first relief cuts 412 defined therein. The raised section 402, and the glove cartridge 400 overall, may exhibit an ovoid or oblong shape, as shown. The oblong shape of the raised section 402 may facilitate installation of the glove 218 and donning of the glove 218 during operation.

FIG. 6 also depicts the retaining whiskers 416 extending across the internal aperture 404 and otherwise stretching across the bottom surface of the raised section 402. As mentioned above, the retaining whiskers 416 may abut an outer surface 504 of the glove 218. The plurality of retaining whiskers 416 may further contact one or more fingers 502 of the glove 218, preventing protrusion of the fingers 502 past the cartridge belt 204. The plurality of retaining whiskers 416 may release or sever as a negative pressure or force from an operator's hand is applied. Following severance or release of the retaining whiskers 416, the outer surface 504 and fingers 502 of the glove 218 may be free to extend and inflate and/or be donned by an operator. The glove 218 may be removed from the glove cartridge 400, and the cartridge belt 204 may be further advanced to provide a new glove cartridge 400 with an installed glove 218 and intact retaining whiskers 416.

Figure 7:
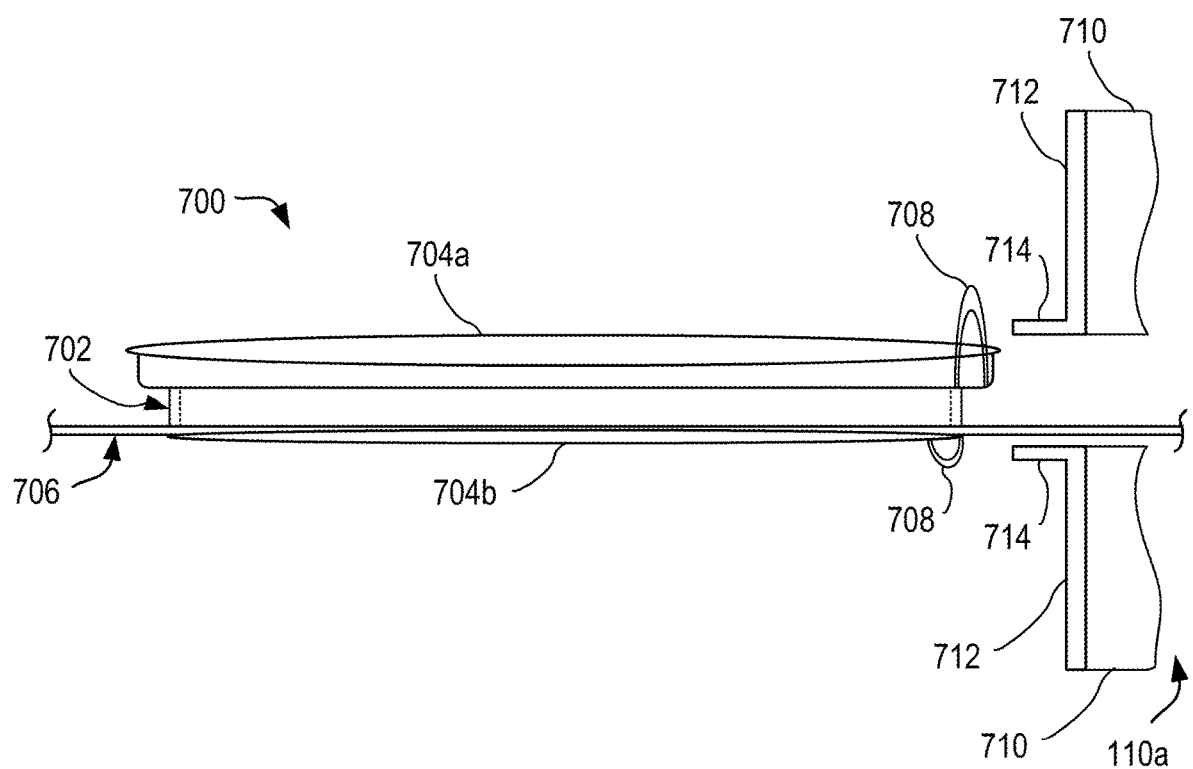
FIG. 7 is a side view of a sealed glove cartridge, according to one or more embodiments of the disclosure.

FIG. 7 is a side view of a glove cartridge 700, according to one or more embodiments of the disclosure. Prior to sealing the glove cartridge 700, a glove (not shown) may be applied to a fastening system 702 of the glove cartridge 700. The fastening system 702 may be similar in some respects to the fastening system 401 of FIGS. 4-6, or of any of the fastening systems 304 described with reference to FIG. 3.

Following application of the glove, a first sealing substrate 704a and a second sealing substrate 704b may be applied to the glove cartridge 700. In at least one embodiment, the sealing substrates 704a,b are formed of a cellophane wrapping. The first sealing substrate 704a may cover and seal any exposed portion of the wrist bead (e.g., the wrist bead 508 of the glove 218 of FIGS. 5-6) and the glove. The second sealing substrate 704b may cover and seal the fingers (e.g., the fingers 502 of FIGS. 5-6) of the glove from below. Both sealing substrates 704a,b may include a tab 708 which may be adhered or otherwise attach to each sealing substrate 704a,b. The tab 708 may be operable to remove the corresponding sealing substrate 704a,b at a desired time or location. In some embodiments, the sealing substrates 704a,b may be retained on the glove cartridge 700 until the cartridge belt 706 nears or reaches the walls 710 of an install cavity 110a.

The walls 710 of the install cavity 110a may include one or more brackets 712 which are positioned near the cartridge belt 706. The brackets 712 may further include a protrusion 714, such as a hook or the like, which may be positioned to engage and catch the tabs 708 as the cartridge belt 706 is fed into the install cavity 110a. The protrusion 714 may advance into an open aperture defined by the tab 708, and continued motion of the cartridge belt 706 may begin the removal process of each sealing substrate 704a,b. As the cartridge belt 706 continues to travel, the sealing substrates 704a,b may begin to peel or tear away from the glove cartridge 700, thus exposing the glove within. As such, from the point of manufacture until reaching the install cavity 110a, the glove (not shown) may be hermetically sealed from any external contaminants.

Figure 8A:
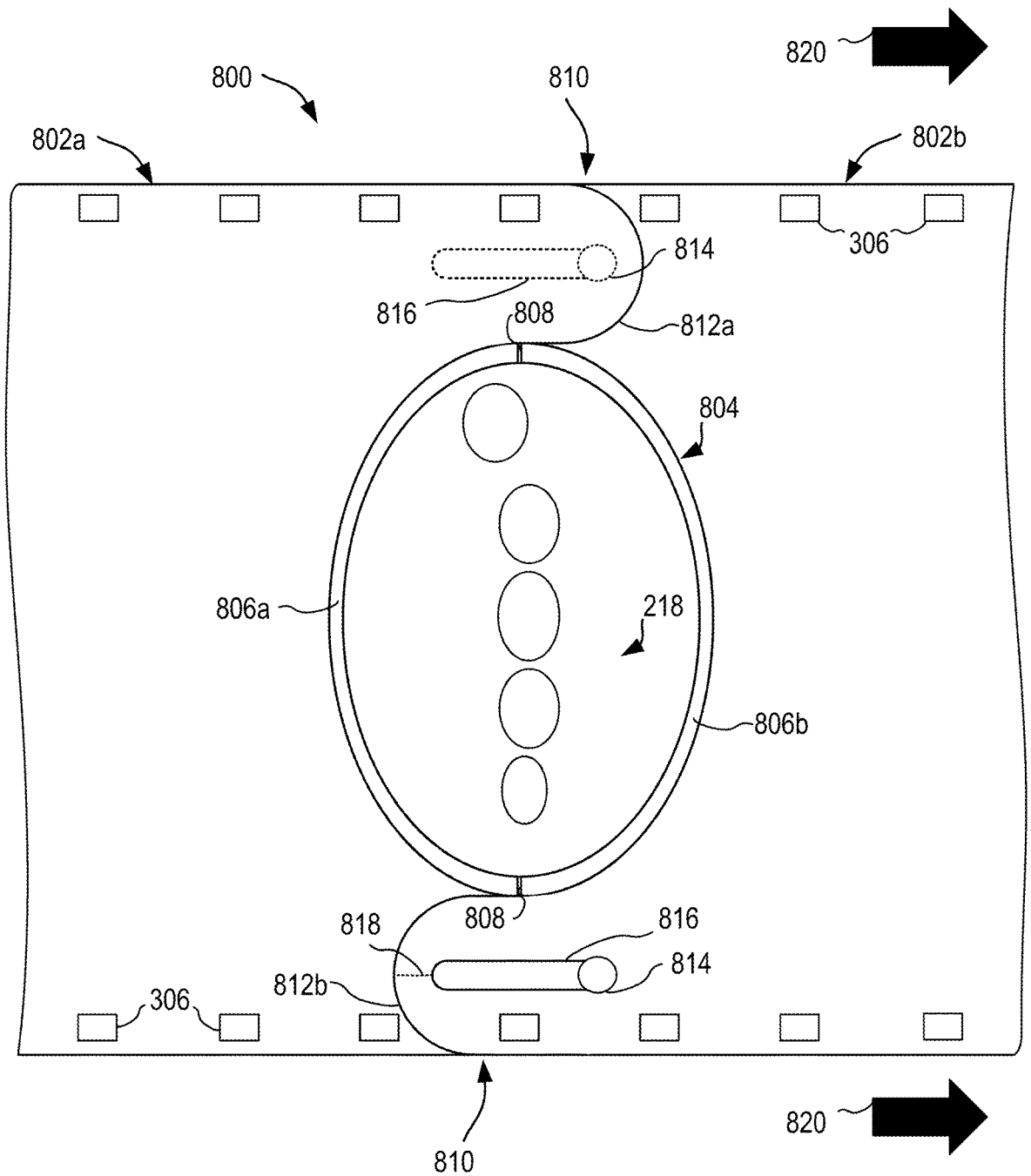
FIG. 8A is a bottom view of a portion of an expandable cartridge belt in a relaxed state, according to one or more embodiments of the disclosure.

FIG. 8A is a bottom view of a portion of an expandable cartridge belt 800 in a relaxed state, according to one or more embodiments of the disclosure. The expandable cartridge belt 800 may be formed of a plurality of first segments 802a and a plurality of second segments 802b which may be mated to form a continuous expandable cartridge belt 800. The plurality of first segments 802a and the plurality of second segments 802b may be formed of a planar strip of flexible material, such as a mechanically durable plastic (e.g., vinyl, polyethylene, etc.), but could alternatively be made of paper or a paper product.

The expandable cartridge belt 800 may include a plurality of fastening systems 804 for attachment of a glove 218, as shown in FIG. 8A. The fastening systems 804 may each span laterally adjacent segments 802a,b and include a first section 806a provided on the plurality of first segments 802a, and a second section 806b provided on the plurality of second segments 802b. The fastening system 804 may be a bipartite form of the fastening system 401 (FIGS. 4-6), or of any of the fastening systems 304 (FIG. 3). As such, the first and second sections 806a,b may utilize a similar mechanism to any previously described fastening systems, with the addition of a separation or gap 808 defined between the first and second sections 806a,b.

Laterally adjacent first and second segments 802a,b may be mated via a connection system 810, shown as overlapping tabs 812a,b in FIG. 8A. It should be noted however, that the connection system 810 may include any connection means, such as a slot, a clip, a pin, or an adhesive, without departing from the scope of this disclosure. In some embodiments, each segment 802a,b includes two tabs 812a,b, which may include further connecting means. In the illustrated embodiment, for example, the first tabs 812a include pins 814 which protrude from the surface of the first tabs 812a. The pins 814 penetrate through corresponding slots 816 defined in the overlapping second tabs 812b and form an interference fit for connecting the first segment 802a to the second segment 802b. In some embodiments, the pins 814 may be adhered within the slots 816 following insertion, such that the segments 802a,b are further mated.

In at least one embodiment, one end of each slot 816 may include a perforated section 818 defined through the end of the tab 812a,b and contiguous with the corresponding slot 816. In such embodiments, the perforated section 818 may be configured to fail and thereby enable the corresponding pin 814 to push through the end of the slot 816 and the corresponding end of the tab 812a,b via the perforated section 818 to release (disengage) the connection system 810 when desired.

The expandable cartridge belt 800 may be stored and transported in the relaxed state, as shown in FIG. 8A, such that the gap 808 is minimal and otherwise negligible, and the fastening system 804 is in a compact state. The expandable cartridge belt 800 may be advanced via gears (e.g., pinion gears 214 of FIG. 2) in this relaxed state until reaching an install cavity (e.g., the install cavity 110a of FIG. 1). Upon being received by an install cavity, the gears may hold the first segment 802a in place, while continuing to pull the second segment 802b in the direction 820. Pulling the second segment 802b in the direction 820 may cause the pins 814 to slide within the slots 816, thus increasing the gap 808 and expanding the glove 218 laterally.

Figure 8B:
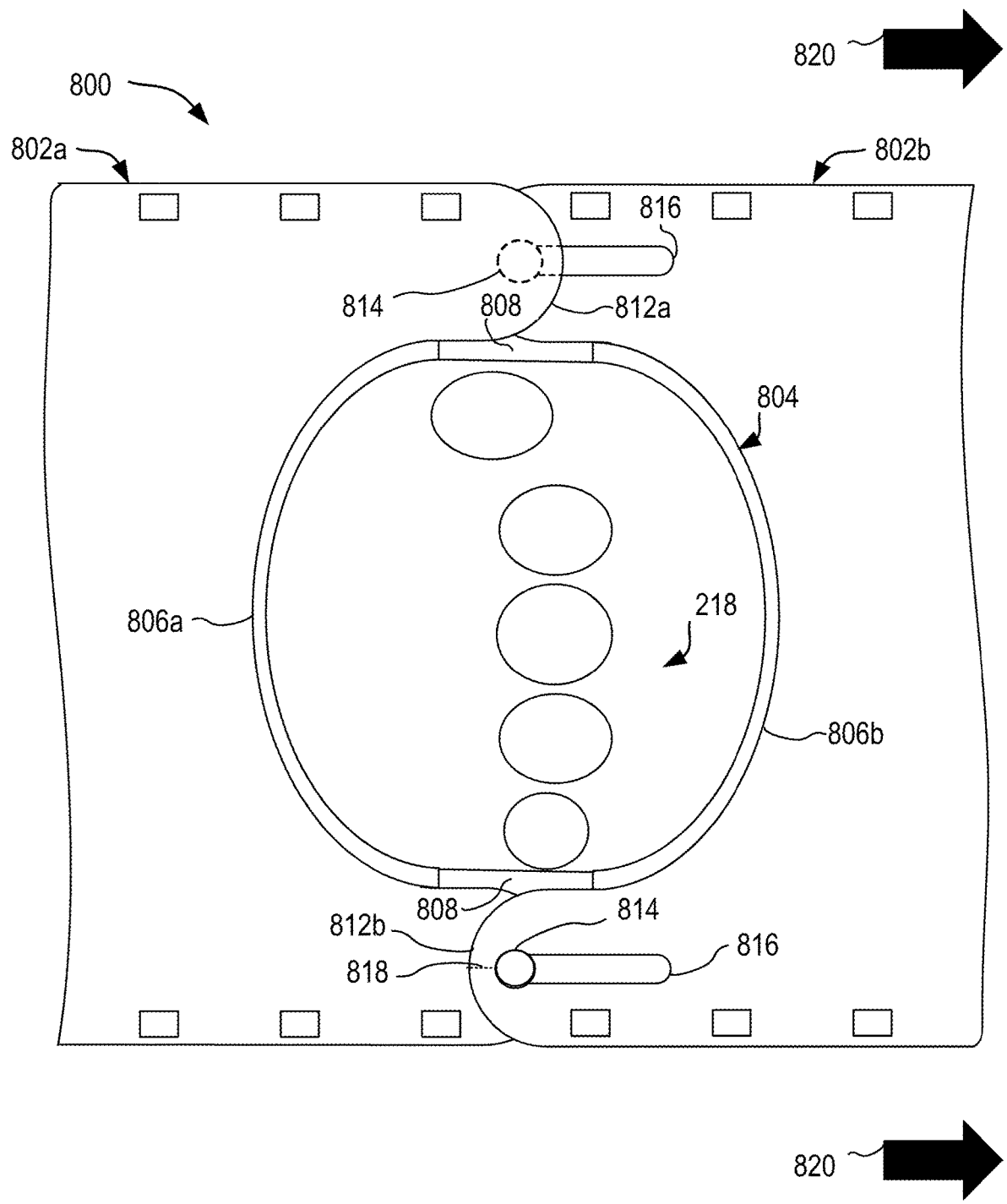
FIG. 8B is a bottom view of a portion of an expandable cartridge belt in an expanded state, according to one or more embodiments of the disclosure.

FIG. 8B is a bottom view of a portion of the expandable cartridge belt 800 in an expanded state, according to one or more embodiments of the disclosure. As the second segment 802b is pulled laterally relative to the first segment 802a, the first and second sections 806a,b will begin to separate and the size of the gap 808 will grow. Moreover, as the first and second sections 806a,b separate, the pins 814 will traverse the length of the slots 816, and once the pins 814 reach the ends of the slots 816, the glove 218 may be in a laterally expanded state. Simultaneously, the install cavity may be expanding the glove 218 into an inflated state. As such, the expandable cartridge belt 800 may enable an operator to insert an ungloved hand into the glove 218 without resistance.

As the glove 218 is seated onto an operator's hand, the added resistance provided by the glove 218 may be removed from the expandable cartridge belt 800. Continued motion of the expandable cartridge belt 800 in the direction 820 may push the pins 814 through the perforated sections of the tabs 812b, thus releasing the second segment 802b from the first segment 802a. In alternate embodiments, however, the expandable cartridge belt 800 may laterally move in the direction 820 and a new fastening system 804 may be aligned with the install cavity.

Embodiments disclosed herein include:

A. A glove application system that includes a glove application module providing a housing that defines an install cavity and an access aperture providing access into the install cavity, a pressure system operable to generate negative pressure in the install cavity, and a glove cartridge assembly mounted to the housing and including a cartridge belt having a plurality of glove cartridges spaced along the cartridge belt, each glove cartridge having a glove releasably secured to the cartridge belt with a fastening system that includes a raised section protruding from the cartridge belt and defining an internal aperture, and a lip laterally protruding from the raised section and sized to receive a wrist bead of the glove, wherein negative pressure generated by the pressure system causes the glove of an aligned glove cartridge to inflate into the install cavity.

B. A glove cartridge belt including a planar strip of flexible material, and a plurality of glove cartridges secured to the planar strip, each glove cartridge including a fastening system that includes a raised section protruding from the planar strip and defining an internal aperture through the planar strip, and a lip laterally protruding from a top of the raised section, wherein the raised section and the lip are sized to receive a wrist bead of a glove.

C. A glove installation system including a glove cartridge including a fastening system that includes a planar strip of flexible material, a raised section protruding from the planar strip and providing an internal aperture defined through the planar strip, and a lip protruding laterally from a top of the raised section, and an assembly arm including a plurality of installation fingers extending from the assembly arm, and one or more actuators operable to actuate the plurality of installation fingers, wherein a wrist bead of a glove is receivable about the plurality of installation fingers, and the one or more actuators are configured to spread the plurality of installation fingers and the wrist bead over the lip and seat the wrist bead below the lip.

D. An expandable glove cartridge belt including a first planar strip of flexible material that includes one or more first tabs defining a lateral slot, and a first section of a fastening system for securing a glove to the expandable glove cartridge belt, and a second planar strip of flexible material including: one or more second tabs overlapping at least a portion of the one or more first tabs and providing a pin receivable within the lateral slot, and a second section of the fastening system positioned laterally adjacent the first section such that a gap is defined therebetween, wherein the expandable glove cartridge belt is transitionable between a relaxed state, where the gap is minimal, and an expanded state, where the first planar strip moves relative to the second planar strip such that a size of the gap grows, and the pin translates through the lateral slot.

Each of embodiments A, B, C, and D may have one or more of the following additional elements in any combination: Element 1: wherein the raised section defines a plurality of relief cuts at an interface between the raised section and the cartridge belt. Element 2: wherein the lip defines a plurality of relief cuts at an interface between the raised section and the lip. Element 3: wherein each glove cartridge further includes a plurality of retaining whiskers extending across the internal aperture. Element 4: wherein the plurality of retaining whiskers is formed from the cartridge belt. Element 5: wherein the plurality of retaining whiskers is adhered or fastened to the cartridge belt or the plurality of glove cartridges. Element 6: further comprising a door arranged at the access aperture and operable to expose the access aperture for a user to access the glove, and occlude the access aperture following the user removing the glove. Element 7: wherein the raised section defines a plurality of relief cuts at an interface between the raised section and the planar strip. Element 8: wherein the lip defines a plurality of relief cuts at an interface between the raised section and the lip. Element 9: wherein the raised section and the lip define a plurality of castellations included within the raised section and exhibiting a sloped or tapered shape. Element 10: wherein each glove cartridge further comprises a plurality of retaining whiskers extending across the internal aperture.

Element 11: wherein the plurality of whiskers is formed from the planar strip. Element 12: wherein the plurality of retaining whiskers is adhered or fastened to the planar strip of the plurality of glove cartridges. Element 13: wherein a plurality of castellations are defined in the raised section and the lip and the plurality of castellations are sized to receive the plurality of installation fingers. Element 14: wherein the plurality of installation fingers are retractable through the plurality of castellations to seat the wrist bead below the lip. Element 15: further comprising a perforated section extending from and contiguous with an end of the slot, the perforated section being configured to fail and allow the pin to pass therethrough when the expandable glove cartridge belt transitions to the expanded state. Element 16: wherein, as the expandable glove cartridge belt transitions from the relaxed state to the expanded state, a wrist bead of the glove is expanded.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The use of directional terms such as above, below, upper, lower, upward, downward, left, right, and the like are used in relation to the illustrative embodiments as they are depicted in the figures, the upward direction being toward the top of the corresponding figure and the downward direction being toward the bottom of the corresponding figure.

What is claimed is:

1. A glove application system, comprising:
    a glove application module providing a housing that defines an install cavity and an access aperture providing access into the install cavity;
    a pressure system operable to generate negative pressure in the install cavity; and
    a glove cartridge assembly mounted to the housing and including a cartridge belt having a plurality of glove cartridges spaced along the cartridge belt, each glove cartridge having a glove releasably secured to the cartridge belt with a fastening system that includes:
        a raised section protruding from the cartridge belt and defining an internal aperture; and
        a lip protruding laterally outward from the raised section and away from the internal aperture, the lip being sized to receive a wrist bead of the glove,
    wherein negative pressure generated by the pressure system causes the glove of an aligned glove cartridge to inflate into the install cavity.

2. The glove application system of claim 1, wherein the raised section defines a plurality of relief cuts at an interface between the raised section and the cartridge belt.

3. The glove application system of claim 1, wherein the lip defines a plurality of relief cuts at an interface between the raised section and the lip.

4. The glove application system of claim 1, wherein each glove cartridge further includes a plurality of retaining whiskers extending across the internal aperture.

5. The glove application system of claim 4, wherein the plurality of retaining whiskers is formed from the cartridge belt.

6. The glove application system of claim 4, wherein the plurality of retaining whiskers is adhered or fastened to the cartridge belt or the plurality of glove cartridges.

7. The glove application system of claim 1, further comprising a door arranged at the access aperture and operable to expose the access aperture for a user to access the glove, and occlude the access aperture following the user removing the glove.

8. The glove application system of claim 1, wherein the cartridge belt includes a planar strip of flexible material to which the plurality of glove cartridges are secured, and wherein the internal aperture is defined through the planar strip.

9. The glove application system of claim 8, wherein the raised section defines a plurality of relief cuts at an interface between the raised section and the planar strip.

10. The glove application system of claim 8, wherein the lip defines a plurality of relief cuts at an interface between the raised section and the lip.

11. The glove application system of claim 8, wherein the raised section and the lip define a plurality of castellations included within the raised section and exhibiting a sloped or tapered shape.

12. The glove application system of claim 8, wherein each glove cartridge further comprises a plurality of retaining whiskers extending across the internal aperture.

13. The glove application system of claim 12, wherein the plurality of retaining whiskers is formed from the planar strip.

14. The glove application system of claim 12, wherein the plurality of retaining whiskers is adhered or fastened to the planar strip or the plurality of glove cartridges.

15. A glove installation system, comprising:
    a glove cartridge including a fastening system that includes:
        a planar strip of flexible material;
        a raised section protruding from the planar strip and providing an internal aperture defined through the planar strip; and
        a lip protruding laterally outward from a top of the raised section and away from the internal aperture; and
    an assembly arm including:
        a plurality of installation fingers extending from the assembly arm; and
        one or more actuators operable to actuate the plurality of installation fingers,
    wherein a wrist bead of a glove is receivable about the plurality of installation fingers, and the one or more actuators are configured to spread the plurality of installation fingers and the wrist bead over the lip and seat the wrist bead below the lip.

16. The glove installation system of claim 15, wherein a plurality of castellations are defined in the raised section and the lip and the plurality of castellations are sized to receive the plurality of installation fingers.

17. The glove installation system of claim 16, wherein the plurality of installation fingers are retractable through the plurality of castellations to seat the wrist bead below the lip.

* * * * *